United States Patent
Miyake et al.

(10) Patent No.: US 8,895,564 B2
(45) Date of Patent: Nov. 25, 2014

(54) BIGUANIDE DERIVATIVE COMPOUND

(75) Inventors: Muneharu Miyake, Funabashi (JP); Tadashi Kusama, Yachiyo (JP); Takashi Masuko, Yachiyo (JP)

(73) Assignee: Nihon University, Tokyo (JP)

( * ) Notice: Subject to any disclaimer, the term of this patent is extended or adjusted under 35 U.S.C. 154(b) by 0 days.

(21) Appl. No.: 13/991,344

(22) PCT Filed: Dec. 1, 2011

(86) PCT No.: PCT/JP2011/077762
§ 371 (c)(1),
(2), (4) Date: Jun. 3, 2013

(87) PCT Pub. No.: WO2012/074040
PCT Pub. Date: Jun. 7, 2012

(65) Prior Publication Data
US 2013/0281464 A1    Oct. 24, 2013

(30) Foreign Application Priority Data
Dec. 2, 2010  (JP) ................... 2010-269512

(51) Int. Cl.
*C07D 241/34* (2006.01)
*C07D 241/28* (2006.01)
*A61K 31/4965* (2006.01)

(52) U.S. Cl.
CPC ............ *C07D 241/34* (2013.01); *C07D 241/28* (2013.01); *A61K 31/4965* (2013.01)
USPC .................................... 514/255.06; 544/407

(58) Field of Classification Search
CPC .................................................... C07D 241/34
USPC ......................................................... 544/407
See application file for complete search history.

(56) References Cited

U.S. PATENT DOCUMENTS

| | | | |
|---|---|---|---|
| 2008/0242680 A1 | 10/2008 | Nukina et al. | |
| 2008/0293740 A1 | 11/2008 | Johnson et al. | |
| 2010/0063322 A1 | 3/2010 | Miyake et al. | |

FOREIGN PATENT DOCUMENTS

| | | |
|---|---|---|
| JP | 2004 262762 | 9/2004 |
| JP | 2006 206490 | 8/2006 |
| JP | 2008 222603 | 9/2008 |
| WO | 2008 059800 | 5/2008 |
| WO | 2008 124496 | 10/2008 |

OTHER PUBLICATIONS

Benveniste, H. et al., "Elevation of the Extracellular Concentrations of Glutamate and Aspartate in Rat Hippocampus During Transient Cerebral Ischemia Monitored by Intracerebral Microdialysis," Journal of Neurochemistry, International Society for Neurochemistry, vol. 43, No. 5, pp. 1369 to 1374, (1984).
Williams, K., "Ifenprodil Discriminates Subtypes of the N-Methyl-D-aspartate Receptor: Selectivity and Mechanisms at Recombinant Heteromeric Receptors," The American Society for Pharmacology and Experimental Therapeutics, Molecular Pharmacology, vol. 44, pp. 851 to 859, (1993).
Parsons, C.G. et al., "Amino-alkyl-cyclohexanes are novel uncompetitive NMDA receptor antagonists with strong voltage-dependency and fast blocking kinetics: in vitro and in vivo characterization," Neuropharmacology, vol. 38, pp. 85 to 108, (1999).
Wemmie, J.A. et al., "The Acid-Activated Ion Channel ASIC Contributes to Synaptic Plasticity, Learning, and Memory," Neuron, vol. 34, pp. 463 to 477, (Apr. 25, 2002).
Gao, J., et al., "Coupling between NMDA Receptor and Acid-Sensing Ion Channel Contributes to Ischemic Neuronal Death," Neuron, vol. 48, pp. 635 to 646, (Nov. 23, 2005).
Xiong, Zhi-Gang, et al., "Neuroprotection in Ischemia: Blocking Calcium-Permeable Acid-Sensing Ion Channels," Cell, vol. 118, pp. 687 to 698, (Sep. 17, 2004).
International Search Report Issued Dec. 27, 2011 in PCT/JP11/77762 Filed Dec. 1, 2011.

*Primary Examiner* — Brian McDowell
(74) *Attorney, Agent, or Firm* — Oblon, Spivak, McClelland, Maier & Neustadt, L.L.P.

(57) ABSTRACT

Provided is a novel compound which simultaneously inhibits both NMDA receptors and ASIC1a, which are associated with neurodegenerative disease and so on, and thus is useful for the prevention and treatment of various nervous system diseases. A biguanide derivative represented by the following general formula (1), a salt thereof, or a hydrate of the derivative or the salt:

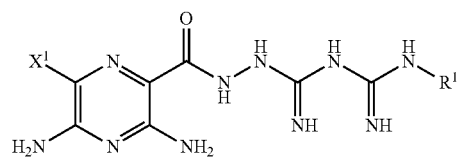

(1)

wherein, $X^1$ represents a halogen atom, $R^1$ represents an alkyl group, an optionally substituted aryl group, or an optionally substituted aralkyl group.

4 Claims, 1 Drawing Sheet

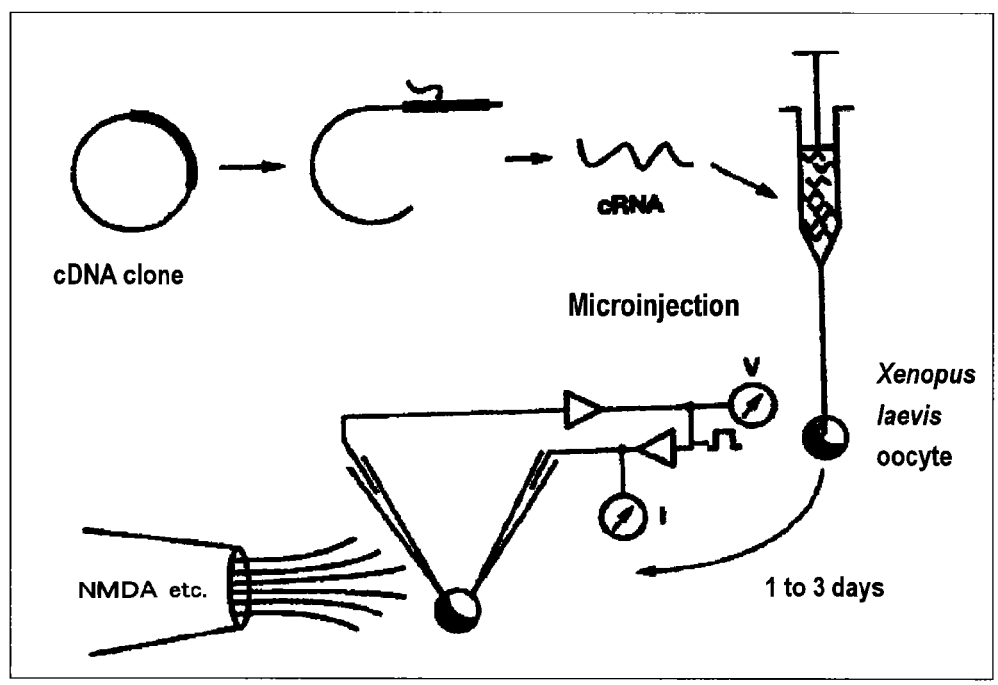

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial sequence
<220> FEATURE:
<223> OTHER INFORMATION: Designed primer based on ASIC1a gene

<400> SEQUENCE: 1
atggaactga aggccgagga g                                          21

<210> SEQ ID NO 2
<211> LENGTH: 24
<212> TYPE: DNA
<213> ORGANISM: Artificial sequence
<220> FEATURE:
<223> OTHER INFORMATION: Designed primer based on ASIC1a gene

<400> SEQUENCE: 2
tcagcaggta aagtcctcga acgt                                       24
```

BIGUANIDE DERIVATIVE COMPOUND

TECHNICAL FIELD

The present invention relates to a biguanide derivative compound, which is useful as a preventive or therapeutic drug for neurodegenerative disease as represented by Alzheimer's disease.

BACKGROUND ART

Glutamic acid functions also as an excitatory neurotransmitter in the body, and is associated with mental disorder and motor dysfunction based on neurodegeneration as observed in brain and spinal cord injury, Alzheimer's disease, Parkinson's disease, amyotrophic lateral sclerosis, Huntington's disease, and so on. Glutamate receptors are classified into N-methyl-D-aspartate (hereinbelow, referred to as "NMDA") receptors; α-amino-3-hydroxy-5-methyl-4-isoxazolepropionic acid (hereinbelow, referred to as "AMPA") receptors and kainate receptors, both of which are non-NMDA receptors; and metabotropic receptors. Glutamate receptors allow the influx of sodium ions and potassium ions into the cells upon activation by glutamic acid or aspartic acid. Particularly, NMDA receptors are known to allow also the influx of calcium ions upon activation. Therefore, while NMDA receptors are associated with the formation of memory and learning, neural development, and so on in the mammalian brain, hyperexcitation of NMDA receptors causes irreversible necrosis of nerve cells in the brain due to the massive influx of calcium into the cells, resulting in damage such as movement disorder, perceptual disorder, and abnormal behavior as a sequel (Non Patent Literatures 1 to 3).

As described above, NMDA receptors are associated with various nervous system diseases, and NMDA receptor inhibitors are expected to serve as therapeutic drugs for these diseases. As NMDA receptor inhibitors, memantine, macrocyclic compounds, and polyamine compounds are reported (Patent Literatures 1 to 3).

Meanwhile, acid-sensing ion channel 1a (ASIC1a) is one of the ion channels, and activation of ASIC1a causes an influx of sodium into the cells, followed by depolarization. Depolarization of the cell membrane promotes activation of NMDA receptors, and the activated NMDA receptors allow the influx of sodium and calcium therethrough. Calcium which has flowed in through NMDA receptors activates the enzyme CaMK II, and the activated CaMK II then mediates phosphorylation of ASIC1. By the phosphorylated ASIC1, the channel activity is promoted (Non Patent Literatures 4 and 5).

As described above, since ASIC1a is one of the channels for sodium and the like, it is associated with diuretic action, neurodegenerative disease, and so on. Amiloride, which is an ASIC1a inhibitor, is not only used as a diuretic drug but also expected to be effective for neurodegenerative disease (Non Patent Literature 6).

CITATION LIST

Patent Literature

[Patent Literature 1] JP-A-2004-262762
[Patent Literature 2] JP-A-2006-206490
[Patent Literature 3] International Publication No. WO2008/059800

Non Patent Literature

[Non Patent Literature 1] Benveniste, H. et al., (1984), J. Neurochem., 43, 1369.

[Non Patent Literature 2] Williams K et al., (1993), Mol. Pharmacol. 44: pp. 851 to 859.
[Non Patent Literature 3] Chris G. Parsons et al., (1999), Neuropharmacology 38: pp. 85 to 108.
[Non Patent Literature 4] Wemmie A. J. et al., (2002), Neuron, 34: pp. 463 to 477.
[Non Patent Literature 5] Gao J. et al., (2005), Neuron, 48: pp. 635 to 646.
[Non Patent Literature 6] Xiong Z.-J. et al., (2004), Cell, 118: pp. 687 to 698.

SUMMARY OF INVENTION

Technical Problem

However, the pharmacological actions of the aforementioned NMDA receptor inhibitor memantine and the aforementioned ASIC1a inhibitor amiloride, are still inadequate, and therefore, there is a demand for the development of better NMDA receptor inhibitors and ASIC1a inhibitors. Meanwhile, a drug inhibiting both NMDA receptors and ASIC1a at the same time has never been reported.

Accordingly, an object of the present invention is to provide a novel compound which simultaneously inhibits both NMDA receptors and ASIC1a which are associated with neurodegenerative disease and so on and thus is useful for the prevention and treatment of various nervous system diseases.

Solution to Problem

In light of the above, the present inventors conducted various studies to search for a compound which inhibits both NMDA receptors and ASIC1a at the same time. As a result, they found that a biguanide compound having a pyrazine skeleton inhibits both NMDA receptors and ASIC1a at the same time, while it is only weakly cytotoxic; and therefore, it is useful as a pharmaceutical product for the prevention and treatment of neurodegenerative disease such as Alzheimer's disease and Parkinson's disease, thereby completing the present invention.

That is, the present invention relates to the following [1] to [16].

[1] A biguanide derivative represented by general formula (1), a salt thereof, or a hydrate of the derivative or the salt:

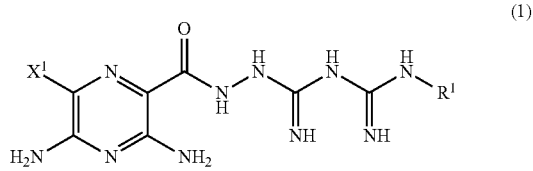

wherein, $X^1$ represents a halogen atom, $R^1$ represents an alkyl group, an optionally substituted aryl group, or an optionally substituted aralkyl group.

[2] The biguanide derivative, a salt thereof, or a hydrate of the derivative or the salt according to [1], wherein $R^1$ represents an alkyl group having 1 to 8 carbon atoms; an aryl group having 6 to 14 carbon atoms optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group; or a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

[3] The biguanide derivative, a salt thereof, or a hydrate of the derivative or the salt according to [1] or [2], wherein $R^1$ represents a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

[4] A pharmaceutical comprising the compound according to any one of [1] to [3].

[5] A pharmaceutical composition comprising the compound according to any one of [1] to [3] and a pharmaceutically acceptable carrier.

[6] The pharmaceutical or pharmaceutical composition according to [4] or [5], wherein the pharmaceutical or pharmaceutical composition is a preventive or therapeutic drug for neurodegenerative disease.

[7] The pharmaceutical or pharmaceutical composition according to [6], wherein the neurodegenerative disease is Alzheimer's disease, Parkinson's disease, or Huntington's disease.

[8] The compound according to any one of [1] to [3], for the prevention or treatment of neurodegenerative disease.

[9] The compound according to [8], wherein the neurodegenerative disease is Alzheimer's disease, Parkinson's disease, or Huntington's disease.

[10] Use of a biguanide derivative represented by general formula (1), a salt thereof, or a hydrate of the derivative or the salt:

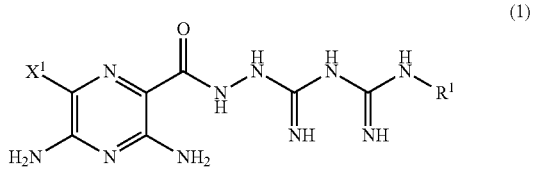

(1)

wherein, $X^1$ represents a halogen atom, $R^1$ represents an alkyl group, an optionally substituted aryl group, or an optionally substituted aralkyl group, for the production of a preventive or therapeutic drug for neurodegenerative disease.

[11] The use according to [10], wherein $R^1$ represents an alkyl group having 1 to 8 carbon atoms; an aryl group having 6 to 14 carbon atoms optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group; or a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

[12] The use according to [10] or [11], wherein $R^1$ represents a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

[13] The use according to [12], wherein the neurodegenerative disease is Alzheimer's disease, Parkinson's disease, or Huntington's disease.

[14] A method for preventing or treating neurodegenerative disease, comprising administering a biguanide derivative represented by general formula (1), a salt thereof, or a hydrate of the derivative or the salt:

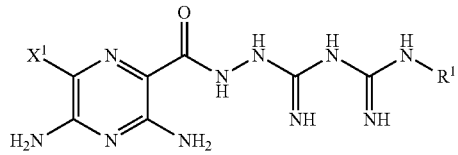

(1)

wherein, $X^1$ represents a halogen atom, $R^1$ represents an alkyl group, an optionally substituted aryl group, or an optionally substituted aralkyl group.

[15] The method according to [14], wherein $R^1$ represents an alkyl group having 1 to 8 carbon atoms; an aryl group having 6 to 14 carbon atoms optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group; or a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

[16] The method according to [14] or [15], wherein $R^1$ represents a $C_{6-14}$ aryl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group.

Advantageous Effects of Invention

The compound (1) of the present invention potently inhibits both NMDA receptors and ASIC1a, while it is only weakly cytotoxic. Hence, the compound (1) of the present invention is useful as a preventive or therapeutic drug for various diseases involving NMDA receptors or ASIC1a, for example, neurodegenerative disease such as Alzheimer's disease, Parkinson's disease, Huntington's disease, brain and spinal cord injury, and amyotrophic lateral sclerosis.

BRIEF DESCRIPTION OF DRAWINGS

FIG. 1 shows a scheme of the NMDA receptor expression system in *Xenopus laevis*.

DESCRIPTION OF EMBODIMENTS

The compound of the present invention is a biguanide derivative represented by the general formula (1) shown above, a salt thereof, or a hydrate of the derivative or the salt.

In the general formula (1), $X^1$ represents a halogen atom. Examples of the halogen atom include a fluorine atom, a chlorine atom, a bromine atom, and an iodine atom. Among them, a chlorine atom is preferable.

$R^1$ represents an alkyl group, an optionally substituted aryl group, or an optionally substituted aralkyl group. Examples of the alkyl group include a linear or branched alkyl group having 1 to 8 carbon atoms, and a linear or branched alkyl group having 1 to 6 carbon atoms is more preferable. Specific examples of the alkyl group include a methyl group, an ethyl group, an n-propyl group, an isopropyl group, an n-butyl group, an isobutyl group, a sec-butyl group, a tert-butyl group, an n-pentyl group, an n-hexyl group, and an n-octyl group.

Examples of the aryl group in the optionally substituted aryl group include a $C_{6-14}$ aryl group, and specific examples include a phenyl group, a naphthyl group, and an anthracenyl group. Among them, a phenyl group and a naphthyl group are preferable, of which a phenyl group is particularly preferable.

Examples of the group with which the aryl group is optionally substituted include 1 to 3 substituent(s) selected from the group consisting of a halogen atom, an alkyl group, an alkoxy group, a nitro group, a hydroxy group, and a halogenoalkyl group. Among them, 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group are preferable. Here, examples of the halogen atom include a fluorine atom, a chlorine atom, a bromine atom, and an iodine atom. Examples of the alkyl group include a methyl group, an ethyl group, an n-propyl group, an isopropyl group, an n-butyl group, an isobutyl group, a sec-butyl group, a tert-butyl group, and an n-pentyl group. Examples of the alkoxy group include a methoxy group, an ethoxy group, an n-propyloxy group, and an isopropyloxy group. Examples of the halogenoalkyl group include a chloromethyl group, a trifluoromethyl group, and a trifluoroethyl group.

Examples of the aralkyl group in the optionally substituted aralkyl group include a $C_{6-14}$ aryl-$C_{1-4}$ alkyl group, and a phenyl-$C_{1-4}$ alkyl group, a naphthyl-$C_{1-4}$ alkyl group, and the like are preferable. Specific examples include a benzyl group, a phenethyl group, a phenylpropyl group, and a phenylbutyl group.

Examples of the group with which the aralkyl group is optionally substituted include 1 to 3 substituent(s) selected from the group consisting of a halogen atom, an alkyl group, an alkoxy group, a nitro group, a hydroxy group, and a halogenoalkyl group. Among them, 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group are preferable. Here, examples of the halogen atom include a fluorine atom, a chlorine atom, a bromine atom, and an iodine atom. Examples of the alkyl group include a methyl group, an ethyl group, an n-propyl group, an isopropyl group, an n-butyl group, an isobutyl group, a sec-butyl group, a tert-butyl group, and an n-pentyl group. Examples of the alkoxy group include a methoxy group, an ethoxy group, an n-propyloxy group, and an isopropyloxy group. Examples of the halogenoalkyl group include a chloromethyl group, a trifluoromethyl group, and a trifluoroethyl group.

Preferable examples of the optionally substituted aryl group represented by $R^1$ include a phenyl group or a naphthyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group. Moreover, a phenyl group or a naphthyl group optionally substituted with 1 to 3 substituent(s) selected from the group consisting of a halogen atom, a methyl group, a methoxy group, a nitro group, a hydroxy group, and a trifluoromethyl group is preferable.

Preferable examples of the optionally substituted aralkyl group represented by $R^1$ include a phenyl-$C_{1-4}$ alkyl group or a naphthyl-$C_{1-4}$ alkyl group optionally substituted with 1 to 3 substituent(s) selected from the group consisting of a halogen atom, a $C_{1-6}$ alkyl group, a $C_{1-6}$ alkoxy group, a nitro group, a hydroxy group, and a $C_{1-6}$ halogenoalkyl group. Moreover, a phenyl-$C_{1-4}$ alkyl group or a naphthyl-$C_{1-4}$ alkyl group optionally substituted with 1 to 3 substituent(s) selected from the group consisting of a halogen atom, a methyl group, a methoxy group, a nitro group, a hydroxy group, and a trifluoromethyl group is preferable.

The salt of the compound (1) of the present invention may be a pharmaceutically acceptable salt, and examples thereof include a salt with an inorganic acid such as sulfuric acid, nitric acid, carbonic acid, bicarbonic acid, hydrobromic acid, and hydriodic acid; a salt with an organic carboxylic acid such as acetic acid, maleic acid, lactic acid, tartaric acid, and trifluoroacetic acid; and a salt with an organic sulfonic acid such as methanesulfonic acid, hydroxymethanesulfonic acid, hydroxyethanesulfonic acid, benzenesulfonic acid, toluenesulfonic acid, and taurine.

A hydrate of the compound (1) of the present invention or a salt thereof is also encompassed by the present invention.

The compound (1) of the present invention can be produced in accordance with, for example, the following reaction formula.

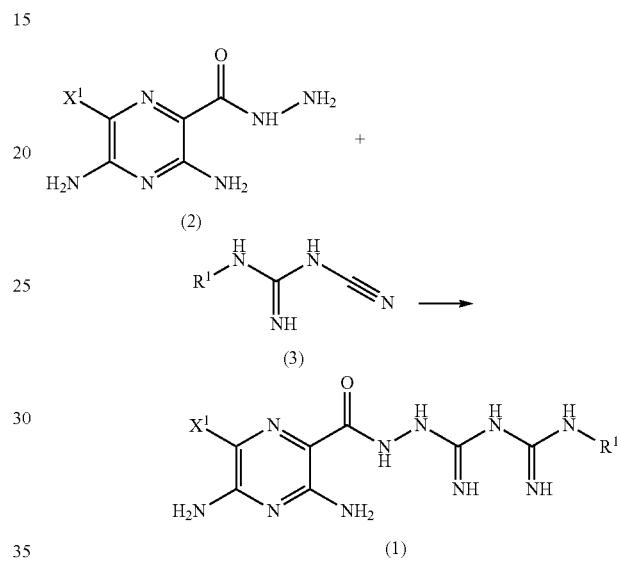

wherein, $X^1$ and $R^1$ have the same meaning as above.

That is, the biguanide derivative (1) of the present invention can be produced by reacting cyanoguanidines (3) with pyrazinecarbohydrazide (2).

Cyanoguanidines (3), which are the raw material compounds, can be obtained by reacting dicyanamide [$NH(CN)_2$] with amine [$R^1$—$NH_2$] (GB599722 (A), U.S. Pat. No. 5,534,565, and EP0161841 (B)).

Reactions of cyanoguanidines (3) with pyrazinecarbohydrazide (2) are preferably carried out in the presence of an acid. Examples of the acid used include hydrochloric acid and sulfuric acid. Reactions are preferably carried out in an organic solvent such as an alcohol solvent, for example ethanol. Reactions may be carried out at from room temperature to solvent reflux temperature.

Upon completion of the reactions, the compound (1) of the present invention can be isolated and purified by means such as washing, recrystallization, and column chromatography.

The interaction between NMDA receptors and ASIC1a has been only recently revealed, and so far, there have been no reports of an attempt to develop a preventive or therapeutic drug for nervous system disease by searching for a compound which inhibits both NMDA receptors and ASIC1a at the same time. With respect to this, the compound (1) of the present invention potently inhibits both NMDA receptors and ASIC1a, and not only that, it is only weakly cytotoxic as will be demonstrated in Examples later. Accordingly, the compound (1) of the present invention is useful as a preventive or therapeutic drug for diseases involving NMDA receptors or ASIC1a, for example, neurodegenerative disease such as Alzheimer's disease, Parkinson's disease, Huntington's disease, brain and spinal cord injury, and amyotrophic lateral sclerosis.

Although the compound (1) of the present invention can be directly used as a pharmaceutical, it can also be used as a pharmaceutical composition with a pharmaceutically acceptable carrier. Examples of the dosage form of such a pharmaceutical composition include an orally administered preparation such as a tablet, a pill, a powder, a granule, a capsule, a lozenge, a syrup, a liquid, an emulsion, and a suspension; and preparations such as an injection; a suppository; an inhalant; a percutaneous absorption agent; an eye drop; and an eye ointment.

When the pharmaceutical composition is provided in the form of a solid preparation, additives such as sucrose, lactose, cellulosic sugar, D-mannitol, maltitol, dextran, starches, agar, alginates, chitins, chitosans, pectins, trant gums, arabic gums, gelatins, collagens, casein, albumin, calcium phosphate, sorbitol, glycine, carboxymethylcellulose, polyvinylpyrrolidone, hydroxypropylcellulose, hydroxypropylmethylcellulose, glycerin, polyethylene glycol, sodium bicarbonate, magnesium stearate, and talc are used. Further, tablets can be subjected to an ordinary coating process and provided in the form of, for example, sugar-coated tablets, enteric coated tablets, film coated tablets, or double-layered tablets or multi-layered tablets.

When the pharmaceutical composition is provided in the form of a semi-solid preparation, animal or plant-derived oil or fat (such as olive oil, corn oil, and castor oil), mineral oil or fat (such as petrolatum, white petrolatum, and solid paraffin), waxes (such as jojoba oil, carnauba wax, and beeswax), partially or wholly synthesized glycerin fatty acid ester (such as lauryl acid, myristic acid, and palmitic acid), and the like are used.

When the pharmaceutical composition is provided in the form of a liquid preparation, examples of the additives include sodium chloride, glucose, sorbitol, glycerin, olive oil, propylene glycol, and ethyl alcohol. Particularly, when the pharmaceutical composition is provided in the form of an injection, a sterile aqueous solution such as physiological saline, an isotonic liquid, and an oily liquid such as sesame oil and soybean oil are used. Also, an appropriate suspending agent such as sodium carboxymethylcellulose, a nonionic surfactant, a solubilizing aid such as benzyl benzoate and benzyl alcohol can be used in combination as needed.

The amount of active ingredient in these preparations is 0.1 to 100% by weight, appropriately 1 to 50% by weight of the preparation. The dose may vary depending on factors such as the symptoms, body weight, and age of the patients. When the preparation is orally administered, normally, the daily dose for an adult is approximately 1 to 500 mg in terms of the compound (1) of the present invention. The above dose is preferably administered all at once or in several divided doses.

EXAMPLES

Example 1

A mixture of 3,5-diamino-6-chloropyrazine-2-carbohydrazide (101 mg, 0.5 mmol), 1-[(2-phenylethyl)]-3-cyanoguanidine (94 mg, 0.5 mmol), ethanol (2 mL), and 5N HCl (0.1 mL, 0.5 mmol) was stirred and heated to reflux for 18 hours. After cooling, the precipitate was filtered off and the filtrate was concentrated under reduced pressure. To the residue, methanol (2 mL) and a 5M NaOMe solution in methanol (0.2 mL) were added to make the solution alkaline. The mixture thus obtained was subjected to silica gel column chromatography and then eluted with $CHCl_3$:methanol:25% $NH_4OH$ (100:40:4) to give 1-(3,5-diamino-6-chloropyrazinamide)-5-[2-(phenylethyl)biguanide (Compound 1) as yellow amorphous powder (120 mg, yield 62%).

$^1$H-NMR (500 MHz, DMSO-$d_6$+$D_2$O) δ: 2.81 (2H, t, J=7.5 Hz), 3.38 (2H, t, J=7.5 Hz), 7.22 (2H, t, J=6.9 Hz), 7.27-7.31 (3H, m).

$^{13}$C-NMR (125 MHz DMSO-$d_6$) δ: 36.59, 43.44, 114.42, 118.32, 127.35, 129.56, 130.03, 140.80, 153.81, 155.36, 158.23, 161.60, 163.42.

HR-FAB-MS m/z: 391.1510[M+H]$^+$ (Calcd for $C_{15}H_{20}{}^{35}ClN_{10}O$: 391.1509), 393.1478[M+H]$^+$ (Calcd for $C_{15}H_{20}{}^{37}ClN_{10}O$: 393.1480).

Example 2

Using 1-[2-(4-chlorophenyl)ethyl]-3-cyanoguanidine instead of 1-[(2-phenylethyl)]-3-cyanoguanidine, 1-(3,5-diamino-6-chloropyrazinamide)-5-[2-(4-chlorophenyl)ethyl] biguanide (Compound 2) was obtained as yellow amorphous powder (86 mg, yield 40%) in a similar manner to Example 1.

$^1$H-NMR (500 MHz, DMSO-$d_6$+$D_2$O) δ: 2.80 (2H, t, J=7.5 Hz), 3.36 (2H, t, J=7.5 Hz), 7.30 (2H, br s), 7.34 (2H, d, J=8.0 Hz).

$^{13}$C-NMR (125 MHz, DMSO-$d_6$) δ: 35.73, 43.27, 113.99, 118.54, 129.47, 131.95, 132.03, 139.73, 154.00, 155.50, 158.39, 161.92, 164.51.

HRMS (FAB) m/z: Calcd for $C_{15}H_{19}{}^{35}Cl_2N_{10}O$: 425.1119 (M+1).

Found: 425.1116 (M+1)$^+$. Calcd for $C_{15}H_{19}{}^{35}Cl^{37}ClN_{10}O$: 427.1090 (M+1). Found: 427.1094 (M+1)$^+$. Calcd for $C_{15}H_{19}{}^{37}Cl_2N_{10}O$: 429.1060 (M+1). Found: 429.1107 (M+1)$^+$.

Example 3

Using 1-[2-(3,4-dichlorophenyl)ethyl]-3-cyanoguanidine instead of 1-[(2-phenylethyl)]-3-cyanoguanidine, 1-(3,5-diamino-6-chloropyrazinamide)-5-[2-(3,4-dichlorophenyl) ethyl]biguanide (Compound 3) was obtained as yellow amorphous powder (144 mg, yield 63%) in a similar manner to Example 1.

$^1$H-NMR (500 MHz, DMSO-$d_6$+$D_2$O) δ: 2.83 (2H, t, J=7.2 Hz), 3.38 (2H, t, J=7.2 Hz), 7.27 (1H, br s), 7.53 (2H, br s).

$^{13}$C-NMR (125 MHz DMSO-$d_6$) δ: 35.45, 42.98, 113.97, 118.48, 129.99, 130.62, 131.61, 132.06, 132.14, 142.10, 153.96, 155.47, 158.38, 161.57, 164.28.

HR-FAB-MS m/z: 459.0735[M+H]$^+$ (Calcd for $C_{15}H_{18}{}^{35}Cl_3N_{10}O$: 459.0729), 461.0736[M+H]$^+$ (Calcd for $C_{15}H_{18}{}^{35}Cl_2{}^{37}ClN_{10}O$: 461.0700), 463.0711[M+H]$^+$ (Calcd for $C_{15}H_{18}{}^{35}Cl^{37}Cl_2N_{10}O$: 463.0671), 465.0660[M+H]$^+$ (Calcd for $C_{15}H_{18}{}^{37}Cl_3N_{10}O$: 465.0641).

Example 4

Using 1-[3-(4-chlorophenyl)propyl]-3-cyanoguanidine instead of 1-[(2-phenylethyl)]-3-cyanoguanidine, 1-(3,5-diamino-6-chloropyrazinamide)-5-[3-(4-chlorophenyl)propyl]biguanide (Compound 4) was obtained as yellow amorphous powder (135 mg, yield 61%) in a similar manner to Example 1.

IR (KBr) cm$^{-1}$: 3471, 3318, 3197, 2935, 1604, 1544, 1498, 1427, 1243.

$^1$H-NMR (DMSO-$d_6$+$D_2$O, 500 MHz,) δ: 1.76 (2H, quintet, J=7.5 Hz), 2.61 (2H, t, J=7.5 Hz), 3.13 (2H, t, J=7.5 Hz), 3.11 (2H, t, J=6.9 Hz), 7.25 (2H, d, J=7.5 Hz), 7.32 (2H, d, J=7.5 Hz).

$^{13}$C-NMR (DMSO-d$_6$, 125 MHz) δ: 32.0, 32.98, 41.31, 114.13, 118.42, 129.46, 131.48, 131.60, 142.01, 153.91, 155.43, 158.61, 161.76, 164.10.

HR-FAB-MS m/z: 439.1276 [M+H]$^+$ (Calcd for C$_{16}$H$_{21}$$^{35}$Cl$_2$N$_{10}$O: 439.1276), 441.1244 [M+H]$^+$ (Calcd for C$_{16}$H$_{21}$$^{35}$Cl$^{37}$ClN$_{10}$O: 441.1246), 443.1284 [M+H]$^+$ (Calcd for C$_{16}$H$_{21}$$^{37}$Cl$_2$N$_{10}$O: 443.1217).

Example 5

Using 1-[2-(3-trifluoromethylphenyl)ethyl]-3-cyanoguanidine instead of 1-[(2-phenylethyl)]-3-cyanoguanidine, 1-(3,5-diamino-6-chloropyrazinamide)-5-[2-(3-trifluoromethylphenyl)ethyl]biguanide (Compound 5) was obtained as yellow amorphous powder (135 mg, yield 59%) in a similar manner to Example 1.

IR (KBr) cm$^{-1}$: 3324, 3205, 1612, 1546, 1504, 1425, 1328, 1241.

$^1$H-NMR (DMSO-d$_6$+D$_2$O, 500 MHz,) δ: 2.90 (2H, t, J=7.5 Hz), 3.39 (2H, t, J=7.5 Hz), 7.53-7.64 (4H, m).

$^{13}$C-NMR (DMSO-d$_6$, 125 MHz) δ: 36.36, 40.96, 115.02, 118.05, (124.09, 124.12 or 124.1, d, J$_{C-F}$=3.8 Hz), (124.56, 126.73, 128.89, 129.94 or 127.81, q, J$_{C-F}$=271.0 Hz), (126.59, 126.62 or 126.0, d, J$_{C-F}$=3.8 Hz), (129.94, 130.18, 130.43, 130.68 or 130.30, q, J$_{C-F}$=31.27 Hz), 130.58, 134.36, 142.49, 153.64, 155.20, 157.98, 161.39, 162.56.

HR-FAB-MS m/z: 459.1382 [M+H]$^+$ (Calcd for C$_{16}$H$_{19}$$^{35}$ClF$_3$N$_{10}$O: 459.1383), 461.1371 [M+H]$^+$ (Calcd for C$_{16}$H$_{19}$$^{37}$ClF$_3$N$_{10}$O: 461.1353).

Examples 6 to 27

Compounds shown in Table 1 were obtained in a similar manner to Examples 1 to 5.

TABLE 1

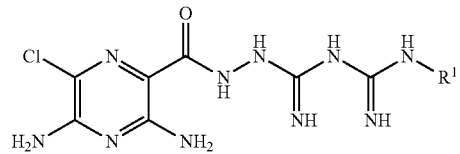

(1)

| Example | R$^1$ |
|---|---|
| 1 | ![phenyl-CH2CH2—] |
| 2 | ![4-Cl-phenyl-CH2CH2—] |
| 3 | ![3,4-diCl-phenyl-CH2CH2—] |
| 4 | ![4-Cl-phenyl-CH2CH2CH2—] |
| 5 | ![3-CF3-phenyl-CH2CH2—] |
| 6 | ![phenyl—] |
| 7 | ![4-CH3O-phenyl—] |
| 8 | ![4-Cl-phenyl—] |
| 9 | ![3-HO-phenyl—] |
| 10 | n-hexyl |
| 11 | ![1-naphthyl—] |
| 12 | ![3,4-diCl-phenyl—] |
| 13 | ![3,4-diCl-phenyl-CH2—] |
| 14 | n-octyl |
| 15 | ![3,4-diF-phenyl—] |
| 16 | ![4-F-phenyl-CH2—] |
| 17 | n-hexyl |
| 18 | n-butyl |

TABLE 1-continued (1)

Cl, H2N-pyrazine core with carboxamide-NH-NH-C(=NH)-NH-C(=NH)-NH-R¹

| Example | R¹ |
|---|---|
| 19 | O₂N—C₆H₄—CH₂— |
| 20 | C₆H₅—CH₂CH₂CH₂— |
| 21 | C₆H₅—CH₂— |
| 22 | Cl—C₆H₄—CH₂— |
| 23 | F₃C—C₆H₄— |
| 24 | F₃C—C₆H₄—CH₂— |
| 25 | n-pentyl |
| 26 | O₂N—C₆H₄—CH₂CH₂— |
| 27 | 3,4-F₂—C₆H₃—CH₂— |

Test Example 1

The effect of the compound of the present invention on NMDA receptors was measured by the two-electrode voltage clamp method.

(1) Preparation of the NMDA receptor-expressing *Xenopus laevis* oocytes

A scheme of the test example for expression in oocytes is shown in FIG. 1. This method can be carried out in accordance with the method of Masuko et al. (Masuko T. et al., Mol. Pharmacol., 55: pp. 957 to 969 (1999); Masuko T. et al., Nuerosci. Lett., 371: pp. 30 to (2004); Masuko T. et al., Chem. Pharm. Bull., 53 (4): pp. 444 to 447 (2005)). Into the oocytes, cRNA of the NR1 subunit and cRNA of the NR2 subunit of the NMDA receptor were injected at a ratio of 1:5 (0.1 to 4 ng of NR1 and 0.5 to 20 ng of NR2), whereby the oocytes expressing NMDA receptors were obtained.

(2) The oocytes thus obtained were cultured in the medium (96 mM NaCl, 2 mM KCl, 1 mM MgCl₂, 1.8 mM CaCl₂, 5 mM Na-HEPES, 2.5 mM sodium pyruvate, 50 mg/mL gentamicin, pH=7.5) at 19° C. for 1 to 3 days.

On the day of measurement, after injecting K⁺-BAPTA into the oocytes, the activity of the receptor was measured by the two-electrode voltage clamp method to be described later using a recording buffer (96 mM NaCl, 2 mM KCl, 1.8 mM BaCl₂, 10 mM Na-HEPES, pH=7.5).

It is to be noted that there is one gene for NR1, while there are four genes for NR2, i.e., NR2A to NR2D, and NMDA receptors include the following subtypes: NR1/NR2A, NR1/NR2B, NR1/NR²C, and NR1/NR2D. Among them, because NR1/NR2A is considered to be most prevalently expressed in the brain, the inhibitory effect on the activity of NR1/NR2A was measured in the following tests.

(3) Two-electrode voltage clamp method

The two-electrode voltage clamp method was carried out in accordance with the method of Masuko et al. (Masuko T. et al., Nuerosci. Lett., 371: pp. 30 to 33 (2004)). Using the two-electrode voltage clamp amplifier CEZ-1250 (NIHON KOHDEN CORPORATION), the electric current which has passed through the entire oocyte membrane was measured. Electrodes were filled with 3M potassium chloride and the resistance was set at 0.4 to 4 MΩ. Also, for measurement, glutamic acid and glycine were added as the NMDA receptor agonists.

(4) To the oocytes obtained by the aforementioned method, various concentrations of compounds were added. Setting the voltage clamp at Vh=−70 mV (resting membrane potential), the inhibitory effect on the activity of NR1/NR2A was measured.

(5) Similar measurement was made using memantine and amiloride as control compounds. The values obtained from four to five oocytes were averaged out and the resulting value ±S.E.M. was obtained as the measurement value. The IC$_{50}$ values obtained from the results are shown in Table 2.

Test Example 2

The effect of the compound of the present invention on ASIC1a was measured by the two-electrode voltage clamp method.

(1) Preparation of the ASIC1a-expressing *Xenopus laevis* oocytes

Using the RNeasy Protect Mini Kit (QIAGEN), total RNA was prepared from HEK293 cells. Subsequently, using the High Fidelity RNA PCR kit (TAKARA BIO INC.), first strand cDNA was synthesized, and using this first strand cDNA as a template, PCR was performed. The sense-strand primer for PCR was: ATGGAACTGAAGGCCGAGGAG (SEQ ID NO: 1) and the antisense-strand primer for PCR was: TCAGCAGGTAAAGTCCTCGAACGT (SEQ ID NO: 2), and the PCR conditions were such that one cycle consisting of 95° C. for 30 seconds, 55° C. for 30 seconds, and 72° C. for 90 seconds was repeated 30 cycles. The PCR product was inserted into the PCR2.1 vector, and the resulting vector was further subcloned into the pcDNA3.1 (−) vector. From the ASIC1a plasmid which was linearized by the BamHI enzyme, capped cRNA was synthesized using the mMessage mMachine Kits (Ambion). The capped cRNA encoding ASIC1a was injected into the oocytes in an amount of 10 ng each, and the resulting oocytes were incubated at 19° C. for 2 to 3 days in the medium (96 mM NaCl, 2 mM KCl, 1 mM MgCl₂, 1.8 mM CaCl₂, 5 mM Na-HEPES, 2.5 mM sodium pyruvate, 50 mg/mL gentamicin, pH=7.5).

(2) For the measurement of the activity of ASIC1a, using a standard extracellular solution (96 mM NaCl, 2 mM KCl, 1.8 mM CaCl₂, 1 mM MgCl₂, 10 mM MES or 5 mM Na-HEPES), the amount of electric current induced by shifting pH from 7.5 to 6.0 was measured by the two-electrode voltage clamp method.

(3) In a similar manner to Test Example 1, the $IC_{50}$ values were obtained from the results obtained using four to five oocytes. The results thus obtained are shown in Table 2.

Test Example 3

Using SH-SY5Y, a cytotoxic test was performed. In this test also, memantine and amiloride were used as control compounds.

The SH-SY5Y neuroblastoma cell line was purchased from American Type Culture Collection. The cells were cultured in the medium containing penicillin (100 U/mL), streptomycin (100 U/mL), and inactivated fetal bovine serum (Gibco). The cells were maintained in a $CO_2$ incubator at 37° C. under the conditions of 95% air and 5% $CO_2$.

Alamar Blue Assay

Undifferentiated SH-SY5Y cells were exposed to various concentrations of Compounds 1, 2, and 3 for 24 hours. The alamar blue stock solution was transferred to a 96-well plate so that the final assay volume was 100 μL/well with a final alamar blue concentration of 10%. Six hours later, reduced alamar blue was measured at a wavelength of 570 nm. As to the survival rate (%), assuming that the mitochondrial respiratory activity in the drug-free cells as 100%, the respiratory activity of the cells exposed to Compounds 1, 2, and 3 for 24 hours was expressed as relative values. The concentrations of Compounds 1, 2, and 3 at which the respiratory activity decreased to 50% are determined as $IC_{50}$ and shown in Table 2.

TABLE 2

| | $IC_{50}$ | | |
|---|---|---|---|
| Compound | ASIC1a | NR1/NR2A | Cytotoxicity |
| Amiloride | 18 μM | 117 μM | 563 μM |
| Memantine | no effect | 0.88 μM | 146 μM |
| Compound 1 | 4.7 μM | 3.5 μM | 2679 μM |

TABLE 2-continued

| | $IC_{50}$ | | |
|---|---|---|---|
| Compound | ASIC1a | NR1/NR2A | Cytotoxicity |
| Compound 2 | 0.49 μM | 0.23 μM | 978 μM |
| Compound 3 | 0.21 μM | 0.30 μM | 277 μM |

Furthermore, the compounds of Examples 4 to 27 described as above were confirmed to have inhibitory activities on ASIC1a and NR1/NR2A at a concentration of 30 μM.

As is apparent from Table 2, the compound of the present invention inhibited NMDA receptors and ASIC1a more potently than amiloride and memantine. Moreover, the cytotoxicity of the compound of the present invention was weak.

The invention claimed is:

1. A compound, wherein the compound is a biguanide derivative of formula (I), a pharmaceutically acceptable salt thereof, or a hydrate of the derivative or the salt:

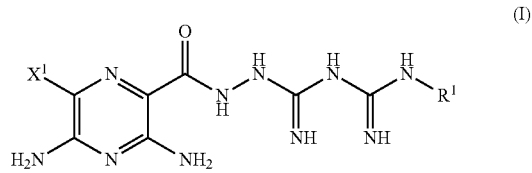

wherein, $X^1$ is a halogen atom, and $R^1$ is an alkyl group, an optionally substituted aryl group, or an optionally substituted aralkyl group.

2. The compound according to claim 1, wherein $R^1$ is an alkyl group comprising 1 to 8 carbon atoms;

an aryl group comprising 6 to 14 carbon atoms optionally substituted with 1 to 3 substituents selected from the group consisting of a halogen atom, a $C_{1-6}$ alkyl group, a $C_{1-6}$ alkoxy group, a nitro group, a hydroxy group, and a $C_{1-6}$ halogenoalkyl group; or a $C_{6-14}$ aryl-$C_{1-4}$ alkyl group optionally substituted with 1 to 3 substituents selected from the group consisting of a halogen atom, a $C_{1-6}$ alkyl group, a $C_{1-6}$ alkoxy group, a nitro group, a hydroxy group, and a $C_{1-6}$ halogenoalkyl group.

3. The compound according to claim 1, wherein $R^1$ is a $C_{6-14}$ aryl-$C_{1-4}$ alkyl group optionally substituted with 1 to 3 substituents selected from the group consisting of a halogen atom, a $C_{1-6}$ alkyl group, a $C_{1-6}$ alkoxy group, a nitro group, a hydroxy group, and a $C_{1-6}$ halogenoalkyl group.

4. A pharmaceutical composition, comprising:
the compound according to claim 1, and
a pharmaceutically acceptable carrier.

* * * * *